US012583972B2

(12) United States Patent
Mahon et al.

(10) Patent No.: US 12,583,972 B2
(45) Date of Patent: Mar. 24, 2026

(54) NON-ISOCYANATE POLYURETHANE ELASTOMERS AND COMPOSITIONS COMPRISING SUCH ELASTOMERS

(71) Applicant: GRANT INDUSTRIES, INC., Elmwood Park, NJ (US)

(72) Inventors: Andrew Bernard Mahon, San Francisco, CA (US); Michael Joseph Isaacman, New York, NY (US); Steven Isaacman, Oak Beach, NY (US)

(73) Assignee: GRANT INDUSTRIES, INC., Elmwood Park, NJ (US)

( * ) Notice: Subject to any disclaimer, the term of this patent is extended or adjusted under 35 U.S.C. 154(b) by 565 days.

(21) Appl. No.: 17/998,365

(22) PCT Filed: May 12, 2021

(86) PCT No.: PCT/US2021/031916

§ 371 (c)(1),
(2) Date: Nov. 10, 2022

(87) PCT Pub. No.: WO2021/231527

PCT Pub. Date: Nov. 18, 2021

(65) Prior Publication Data

US 2023/0183423 A1 Jun. 15, 2023

Related U.S. Application Data

(60) Provisional application No. 63/023,372, filed on May 12, 2020.

(51) Int. Cl.

| | |
|---|---|
| ***A61K 8/87*** | (2006.01) |
| ***A61K 8/04*** | (2006.01) |
| ***A61Q 17/04*** | (2006.01) |
| ***C08G 71/04*** | (2006.01) |
| ***C08L 75/04*** | (2006.01) |
| *A61K 9/00* | (2006.01) |

(52) U.S. Cl.

CPC .............. *C08G 71/04* (2013.01); *A61K 8/042* (2013.01); *A61K 8/87* (2013.01); *A61Q 17/04* (2013.01); *C08L 75/04* (2013.01); *A61K 9/0014* (2013.01); *A61K 2800/805* (2013.01)

(58) Field of Classification Search

None

See application file for complete search history.

(56) References Cited

U.S. PATENT DOCUMENTS

| | | | |
|---|---|---|---|
| 7,045,577 B2 | 5/2006 | Wilkes et al. | |
| 2013/0323491 A1 | 12/2013 | Takahashi et al. | |
| 2014/0030526 A1 | 1/2014 | Uruno et al. | |
| 2015/0110981 A1* | 4/2015 | Dudik | C09D 175/08 524/612 |
| 2017/0218124 A1 | 8/2017 | Faurecia et al. | |

FOREIGN PATENT DOCUMENTS

| | | | |
|---|---|---|---|
| CN | 101808618 | A | 8/2010 |
| CN | 105001400 | A | 10/2015 |
| EP | 3018163 | A1 | 5/2016 |
| WO | 9965969 | A1 | 12/1999 |
| WO | 2009042732 | A1 | 4/2009 |
| WO | 2021/007489 | A1 | 1/2021 |
| WO | 2021067976 | A1 | 4/2021 |

OTHER PUBLICATIONS

Bourguignon; Fast and Facile One-Pot One-Step Preparation of Nonisocyanate Polyurethane Hydrogels in Water at Room Temperature; ACS Sustainable Chemistry & Engineering 2019, 7 pp. 12601-12610. (Year: 2019).*

Extended European Search Report for Corresponding European Application No. 21804576.3, Aug. 27, 2024, 12 Pages.

Feng Yuelan, et al., "Study on the Synthesis of Cyclic Carbonates and NIPU from Epoxidized Soybean Oil and CO2", Polyurethane Industry, vol. 32, issue 1, pp. 1-8, with machine translation, 2017.

Office Action for Corresponding Chinese Patent Application No. 202180047611X, May 25, 2024, 12 pages, with English translation.

International Search Report and Written Opinion in PCT/US2021/031916, dated Sep. 30, 2021.

Beniah et al., "Novel Thermoplastic Polyhydroxyurethane Elastomers as Effective Damping Materials over Broad Temperature Ranges," European Polymer Journal 84:770-783 (2016).

Ke et al., "Non-isocyanate polyurethane/epoxy hybrid materials with different and controlled architectures prepared from a CO2-sourced monomer and epoxy via an environmentally-friendly route," RSC Advances 7:28841-28852 (2017).

* cited by examiner

*Primary Examiner* — David J Buttner

(74) *Attorney, Agent, or Firm* — LUCAS & MERCANTI, LLP

(57) ABSTRACT

The present disclosure relates to gel compositions of, or containing, a non-isocyanate polyurethane (NIPU) elastomer formed from the reaction of a polycarbonate, where carbonate groups may be cyclic or non-cyclic, and a polyamine, where amines are either primary or secondary, in an optional topically acceptable carrier fluid. The gelled compositions may further contain a personal or healthcare active. The actives may be incorporated into the gel via either a pre or post load method.

8 Claims, No Drawings

NON-ISOCYANATE POLYURETHANE ELASTOMERS AND COMPOSITIONS COMPRISING SUCH ELASTOMERS

TECHNICAL FIELD

This invention relates to gel compositions containing a NIPU elastomer from the reaction of a polycyclic or poly-non-cyclic carbonate and a polyamine, and may optionally utilize a catalyst to increase the rate of formation of the elastomer, and is suitably contained in a topically acceptable carrier fluid to form a gel. The gel compositions may contain a personal or healthcare active. The actives may be incorporated into the gel via either a pre or post load method. Gel compositions may be further used as components in personal care compositions.

BACKGROUND

Silicone elastomers have been used extensively in personal care applications for their thickening and gelling efficiency, and unique silky and powdery sensory profile. Silicone elastomers are compatible with silicone-based fluids, however, silicone based fluids for topical use are being phased out of the personal care industry due to health and environmental concerns. There is a need to develop alternatives to silicone elastomers which demonstrate efficient thickening and gelling capabilities with non-silicone based topically acceptable solvents (e.g., esters, triglycerides, and alkanes) while imparting a silky and powdery skin feel comparable to silicone elastomers. Polyurethane elastomers can potentially satisfy this need and provide desirable alternatives to silicone elastomers. Non-isocyanate polyurethane (NIPU) elastomers offer an environmentally friendly alternative to isocyanate derived polyurethanes, which require starting materials synthesized from toxic precursors.

SUMMARY

This disclosure relates to a gel composition comprising a non-isocyanate polyurethane NIPU (NIPU) elastomer from the reaction of:

A) a polycarbonate, where the carbonate groups are either cyclic or non-cyclic, which may optionally contain siloxanes in its backbone, B) a polyamine, where the amine groups are either primary or secondary, C) an optional reaction catalyst, D) an optional topically acceptable carrier fluid, wherein the topically acceptable carrier fluid is a reaction solvent or wherein the topically acceptable carrier fluid is added to the reaction after elastomer formation.

A personal care or healthcare active (E) may be incorporated into the NIPU elastomer gel by dissolving it in the topically acceptable solvent during the formation of the NIPU elastomer gel (pre-load method) or admixing it with a formed NIPU elastomer gel (post-load method).

The invention is directed to the following:

A cross-linked NIPU elastomer network with the following general structure:

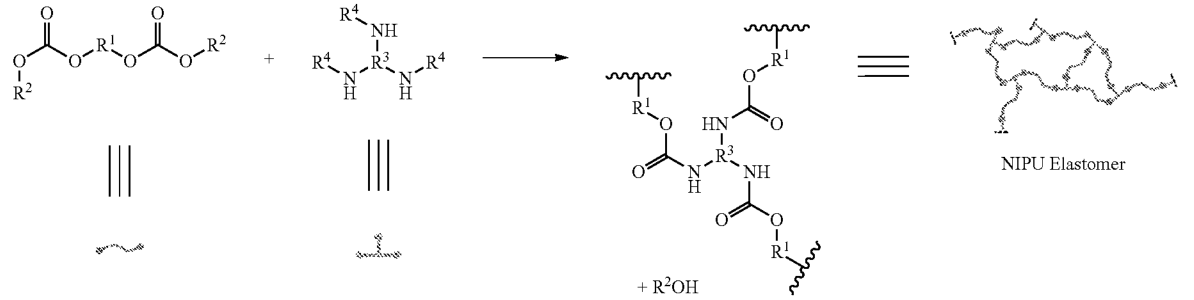

where $R^1$ is an aromatic ring, heterocycle, cyclic alkyl group, linear alkyl group, or branched alkyl group with two or more carbonate functional groups and where $R^2$ is a hydrogen atom, heteroatom, aromatic ring, heterocyclic ring, or alkyl chain. $R^3$ is an aromatic ring, heterocycle, cyclic alkyl group, linear alkyl group, or branched alkyl group with two or more primary or secondary amines. $R^4$ is a hydrogen atom, heteroatom, aromatic ring, heterocycle, cyclic alkyl group, or linear alkyl chain.

A cross-linked NIPU elastomer network with the following general structure:

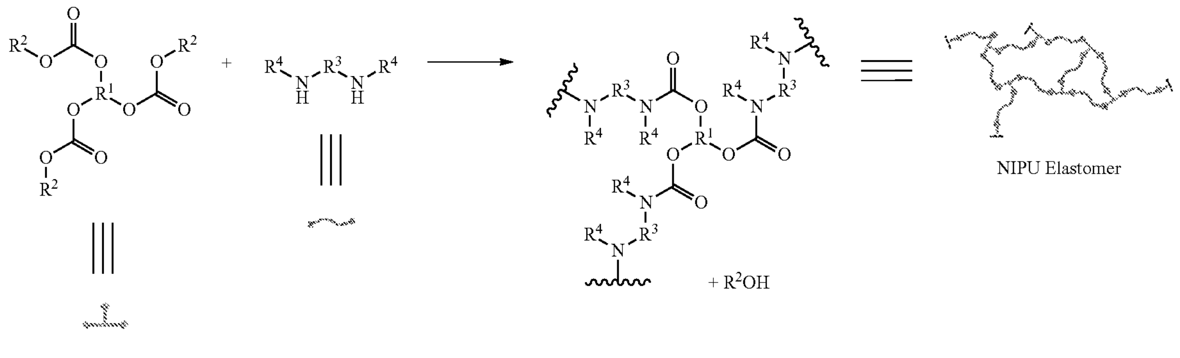

where $R^1$ is an aromatic ring, heterocycle, cyclic alkyl group, linear alkyl group, or branched alkyl group with three or more carbonate functional groups and where $R^2$ is a hydrogen atom, heteroatom, aromatic ring, heterocyclic ring, or alkyl chain. $R^3$ is an aromatic ring, heterocycle, cyclic alkyl group, linear alkyl group, or branched alkyl group with two or more primary or secondary amines. $R^4$ is a hydrogen atom, heteroatom, aromatic ring, heterocycle, cyclic alkyl group, or linear alkyl chain.

A cross-linked NIPU elastomer network with the following general structure:

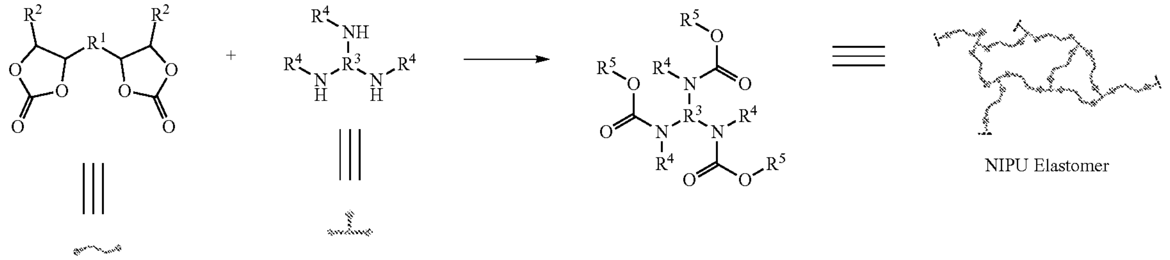

$R^5$ = 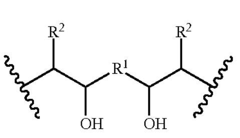 or 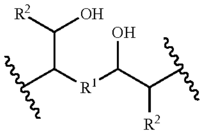 or 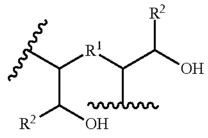

where $R^1$ is an aromatic ring, heterocycle, cyclic alkyl group, linear alkyl group, or branched alkyl group with three or more cyclic carbonate groups and where $R^2$ is a hydrogen atom, heteroatom, aromatic ring, heterocyclic ring, or alkyl chain. $R^3$ is an aromatic ring, heterocycle, cyclic alkyl group, linear alkyl group, or branched alkyl group with two or more primary or secondary amines. $R^4$ is a hydrogen atom, heteroatom, aromatic ring, heterocycle, cyclic alkyl group, or linear alkyl chain.

A cross-linked NIPU elastomer network with the following general structure:

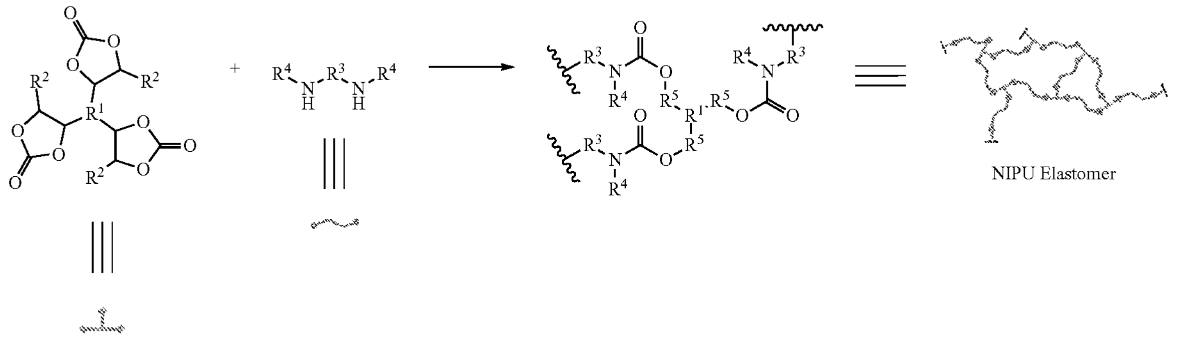

$R^5$ = 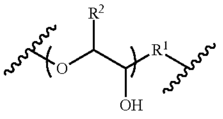 or 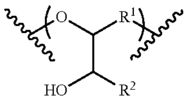

where $R^1$ is an aromatic ring, heterocycle, cyclic alkyl group, or linear or branched alkyl group with three or more cyclic carbonate functional groups and where $R^2$ is a hydrogen atom, heteroatom, aromatic ring, heterocyclic ring, or alkyl chain. $R^3$ is an aromatic ring, heterocycle, cyclic alkyl group, linear alkyl group, or branched alkyl group with two or more primary or secondary amines. $R^4$ is a hydrogen atom, heteroatom, aromatic ring, heterocycle, cyclic alkyl group, or linear alkyl chain.

DETAILED DESCRIPTION

This disclosure relates to a gel composition comprising a polyurethane elastomer requiring no purification and formed in a topically acceptable solvent from the reaction of:

(A) A polycarbonate.

Component (A) has a molecular structure containing more than one cyclic or non-cyclic carbonate and can be produced by a number of methods from alkenes, alkynes, epoxides, vicinal diols, isolated hydroxyl groups, 2-halo alcohols, among others, and should have two or more reactive carbonate functional groups in its molecular structure. One preferred example of a polycarbonate is based on castor oil and has the following structure:

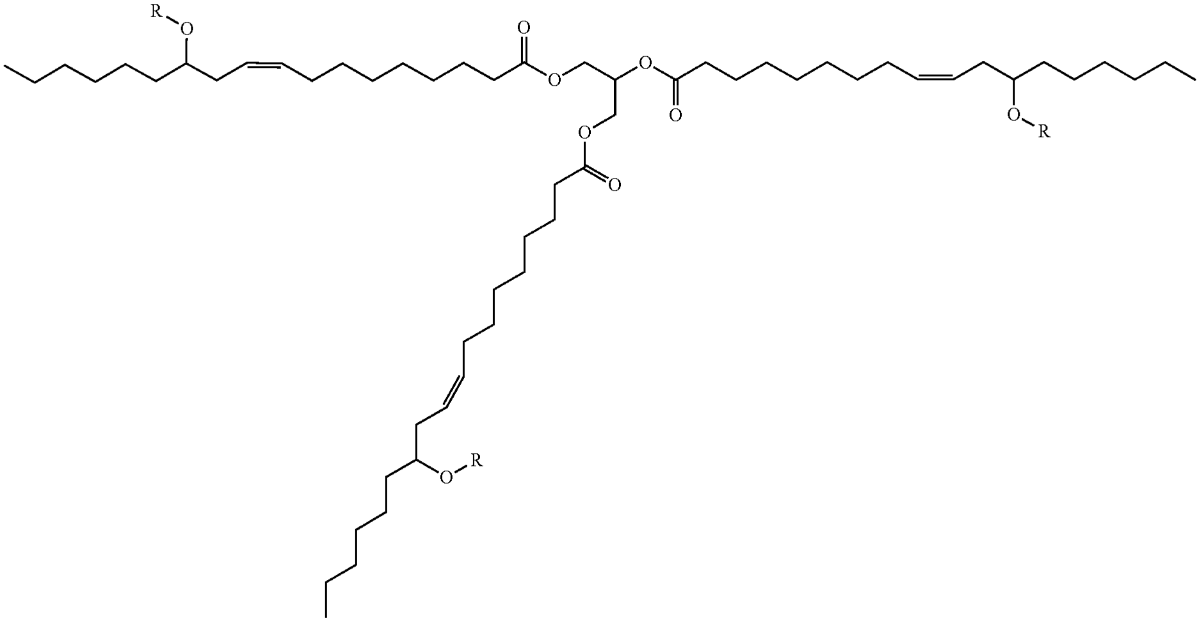

where R contains a cyclic or non-cyclic carbonate.

Another preferred example of a polycarbonate is based on dilinoleic acid/propanediol copolymer and has the following structure:

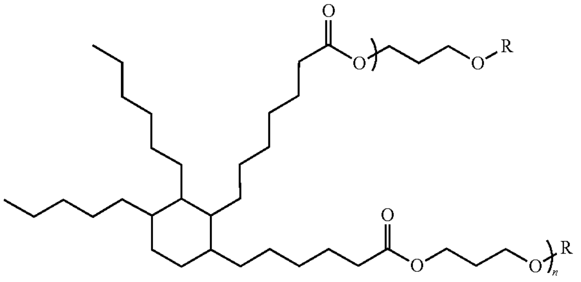

where R contains a cyclic or non-cyclic carbonate.

Another preferred example of a polycarbonate is based on dilinoleic acid/dilinoleic diol copolymer and has the following structure:

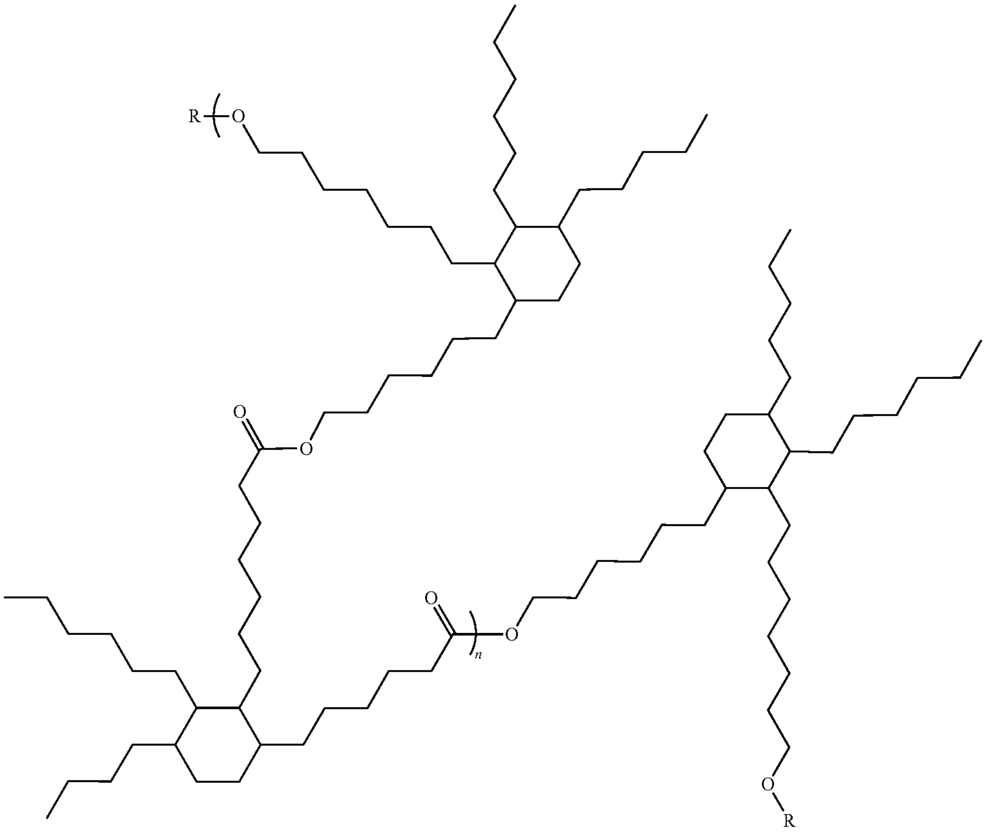

where R contains a cyclic or non-cyclic carbonate.

Component (A) can include one or more functional groups in its polymeric chain. In one aspect, the polycarbonate includes one or more siloxane in its polymeric chain, e.g., in the polymer backbone.

(B) A polyamine, where the amine groups are either primary or secondary.

Component (B) has a molecular structure containing more than one primary or secondary amines. One preferred example of an aliphatic polyamine is hexamethylenediamine and has the structure:

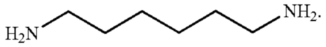

Another preferred example of an aliphatic polyamine is isophorone diamine and has the structure:

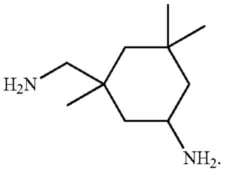

Another preferred example of an aliphatic polyamine is bis(hexamethylene)triamine and has the structure:

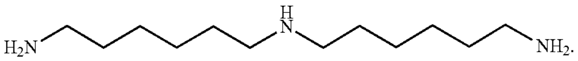

Another preferred example of an aliphatic polyamine is tris(aminoethyl)amine and has the structure:

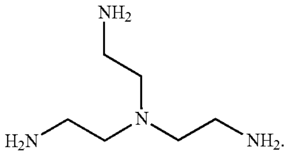

One preferred example of an aromatic polyamine is melamine and has the structure:

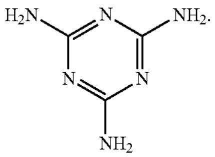

(C) An optional reaction catalyst.

Component (C) can be optionally used to increase the rate of NIPU elastomer formation. Titanium alkoxide are preferred catalysts for the synthesis of NIPU elastomer gels due to their favorable toxicity profile and acceptable use in topical products. Preferably, titanium isopropoxide is used as the NIPU catalyst. Zinc, tin, bismuth, and amine based NIPU catalysts can also be used. Appropriate NIPU catalysts include but are not limited to:

Triethylenediamine
- N,N,N',N",N"-Pentamethyldiethylenetriamine
- 1,2-Dimethylimidazole
- N,N,N',N'-Tetramethyl-1,6-hexanediamine
- N,N',N'-Trimethylaminoethylpiperazine
- 1,1'-[[3-(dimethylamino)propyl]imino]bispropan-2-ol
- N,N,N'-Trimethylaminoethylethanolamine
- N,N',N"-Tris(3-dimethylaminopropyl)-hexahydro-s-triazine
- 1,4-diazabicyclo[2.2.2]octane
- 1,5,7-Triazabicyclo[4.4.0]dec-5-ene
- Stannous octoate
- Stannous oxalate
- Stannous oxide
- Stannous chloride
- Dioctyltin di(2-hexylhexanoate)-solution
- Dioctyltin dithioglycolate
- Dioctyltin dilaurate
- Dioctyltin oxide blend
- Dibutyltin dilaurate
- Monobutyl tin tris-(2-ethylhexanoate)
- Dioctyltin diketanoate
- Dioctyltin diacetate
- Dioctyltin oxide
- Dibutyltin diacetate
- Modified dibutyltin diacetate
- Dibutyltin oxide
- Monobutyltin dihydroxychloride
- Organotin oxide
- Monobutyltin oxide
- Dioctyltin dicarboxylate
- Dioctyltin carboxylate
- Dioctyltin stannoxane
- Zinc neodecanoate
- Zinc octoate
- Zinc acetylacetonate
- Zinc oxalate
- Zinc acetate
- Bismuth carboxylates
- Zinc neodecanoate (D) A Carrier Fluid.

The NIPU elastomers may be contained in an optional carrier fluid (D). Carrier fluids include any suitable solvent that can be used to prepare the NIPU elastomers. In exemplary embodiments, the carrier fluid is a "topically acceptable carrier fluid" which is a solvent for topical use on cutaneous surfaces i.e. skin, lips, mucous membranes, etc. Although it is not required, typically the carrier fluid may be the same as the solvent used for conducting the elastomer reaction as described above. The carrier fluid used for the synthesis of the NIPU elastomer rubber and gel can be fully, partially, or not biobased. The carrier fluid, including a topically acceptable carrier fluid, preferably has a viscosity between 1-65 mPas at 20° C. The spreading value of the carrier fluid, including the topically acceptable carrier fluid, is preferably between 500-2500 $mm^2/10$ min. Appropriate topically acceptable carrier fluids for the synthesis of the NIPU elastomer rubber and processing of the NIPU elastomer gel include but are not limited to esters, triglycerides, hydrocarbons, silicone fluids, and combinations thereof, and include:

- Bis-Diglyceryl Polyacyladipate-1
- Bis-Diglyceryl Polyacyladipate-2
- Butylene Glycol Dicaprylate/Dicaprate
- Butyrospermum Parkii Butter
- Caprylic/Capric Glycerides
- Caprylic/Capric Triglyceride
- Caprylic/Capric/Myristic/Stearic Triglyceride
- Caprylic/Capric/Succinic Triglyceride
- Caprylyl Methicone
- Coco-Caprylate/Caprate
- Decamethylcyclopentasiloxane
- Decyl Oleate
- Dimethiconol
- Diphenylsilanediol
- Dodecamethylcyclohexasiloxane
- Ethyl trisiloxane
- Glyceryl Caprylate
- Glyceryl Citrate/Lactate/Linoleate/Oleate
- Glyceryl Cocoate
- Glyceryl Isostearate
- Glyceryl Oleate
- Glyceryl Ricinoleate
- Glyceryl Ricinoleate, Tocopherol
- Glyceryl Stearate
- Glyceryl Stearate Citrate
- Hexamethyldisilazane
- Hexamethyldisiloxane
- Hydrogenated Coco-Glycerides
- Hydrogenated Palm Oil
- Hydroxytrimethylsilane
- Isopropoxytrimethylsilane
- Methylheptyl Isostearate
- Octamethylcyclotetrasiloxane
- Oleyl Erucate
- Olus Oil
- Organo-modified Siloxanes
- Organosilicone Fluids
- PCA Glyceryl Oleate
- PEG-6 Caprylic/Capric Glycerides
- Phenyltrichlorosilane
- Poly(dimethyl siloxane)
- Poly(ethylene glycol)-containing siloxanes
- Polydimethylsiloxane
- Polyglyceryl-2 Caprate Polyglyceryl-3 Caprate
Polyglyceryl-3 Diisostearate
Polyglyceryl-3 Polyricinoleate
Polyglyceryl-4 Cocoate
Propylene Carbonate
Propylene Glycol Dicaprylate/Dicaprate
Silicone oil
Stearalkonium Bentonite
Stearalkonium Hectorite
Triheptanoin
TriMethyl(broModifluoroMethyl)silane
Trimyristin
Tristearin (E) The Active.

Component (E) is a "pharmaceutically active ingredient," and suitably an active selected from any personal active ingredient or health care active ingredient. As used herein, a "personal care active ingredient" means any compound or mixtures of compounds that are known in the art as additives in the personal care formulations that are typically added for the purpose of treating skin, lips or to provide a cosmetic and/or aesthetic benefit. A "healthcare active ingredient" means any compound or mixtures of compounds that are known in the art to provide a pharmaceutical or medical benefit. Thus, "healthcare active ingredient" includes materials considered an active ingredient or active drug ingredient as generally used and defined by the United States Department of Health & Human Services Food and Drug Administration, contained in Title 21, Chapter I, of the Code of Federal Regulations, Parts 200-299 and Parts 300-499. Thus, pharmaceutically active ingredient can include any component that is intended to furnish pharmacological activity or other direct effect in the diagnosis, cure, mitigation, treatment, or prevention of disease, or to affect the structure or any function of the body of a human or other animals. The phrase can include those components that may undergo chemical change in the manufacture of drug products and be present in drug products in a modified form intended to furnish the specified activity or effect.

Some representative examples of pharmaceutically active ingredients include; drugs, vitamins, minerals; hormones; topical antimicrobial agents such as antibiotic active ingredients, antifungal active ingredients for the treatment of athlete's foot, jockitch, or ringworm, and acne active ingredients; astringent active ingredients; deodorant active ingredients; wart remover active ingredients; corn and callus remover active ingredients; pediculicide active ingredients for the treatment of head, pubic (crab), and body lice; active ingredients for the control of dandruff, seborrheic dermatitis, or psoriasis; and Sunburn prevention and treatment agents.

Useful pharmaceutically active ingredients for use in processes according to the invention include Vitamins and its derivatives, including "pro-vitamins". Vitamins useful herein include, but are not limited to, Vitamin A, retinol, C—C esters of retinol, Vitamin E, tocopherol, esters of vitamin E, and mixtures thereof. Retinol includes trans-retinol, 1.3-cis-retinol, 11-cis-retinol, 9-cis-retinol, and 3,4-didehydro-retinol, Vitamin C and its derivatives, Vitamin B, Vitamin B. Pro Vitamin B5, panthenol, Vitamin B. Vitamin B2, niacin, folic acid, biotin, and pantothenic acid. Other suitable vitamins and the INCI names for the vitamins considered included herein are ascorbyl dipalmitate, ascorbyl methylsilanol pectinate, ascorbyl palmitate, ascorbyl Stearate, ascorbyl glucoside, sodium ascorbyl phosphate, sodium ascorbate, di sodium ascorbyl sulfate, potassium (ascorbyl/tocopheryl)phosphate.

Retinol, it should be noted, is an International Nomenclature Cosmetic Ingredient Name (INCI) designated by The Cosmetic, Toiletry, and Fragrance Association (CTFA), Washington D.C., for vitamin A. Other suitable vitamins and the INCI names for the vitamins considered included herein are retinylacetate, retinyl palmitate, reti nyl propionate, o-tocopherol tocopher solan, tocopheryl acetate, tocopheryl linoleate, tocopheryl nicotinate, and tocopheryl succinate.

The pharmaceutically active ingredient used in processes according to the invention can be an active drug ingredient. Representative examples of some suitable active drug ingredients which can be used are hydrocortisone, ketoprofen, timolol, pilocarpine, adriamycin, mitomycin C, morphine, hydromorphone, diltiazem, theophylline, doxorubicin, daunorubicin, heparin, penicillin G, carbenicillin, cephalothin, cefoxitin, cefotaxime, 5-fluorouracil, cytarabine, 6-azauridine, 6-thioguanine, vinblastine, Vincristine, bleomycin sulfate, aurothioglucose, suramin, mebendazole; clonidine, scopolamine, propranolol, phenylpropanolamine hydrochloride, ouabain, atropine, haloperidol, isosorbide, nitroglycerin, ibuprofen, ubiquinones, indomethacin, prostaglandins, naproxen, Salbutamol, guanaben Z, labetalol, pheniramine, metrifonate, and steroids.

Considered to be included herein as active drug ingredients for purposes of the present invention are antiacne agents such as benzoyl peroxide and tretinoin; antibacterial agents such as chlorohexadiene gluconate; antifungal agents such as miconazole nitrate; anti-inflammatory agents; corticosteroidal drugs; non-steroidal anti-inflammatory agents such as diclofenac; antipsoriasis agents such as clobetasol propionate; anesthetic agents such as lidocaine; antipruritic agents; antidermatitis agents; and agents generally considered barrier films.

The active component E) of the present invention can be a protein, such as an enzyme. The internal inclusion of enzymes in the NIPU elastomer gel have advantages to prevent enzymes from deactivating and maintain bioactive effects of enzymes for longer time. Enzymes include, but are not limited to, commercially available types, improved types, recombinant types, wild types, variants not found in nature, and mixtures thereof. For example, suitable enzymes include hydrolases, cutinases, oxidases, transferases, reductases, hemicellulases, esterases, isomerases, pectinases, lactases, peroxidases, laccases, catalases, and mixtures thereof. Hydrolases include, but are not limited to, proteases (bacterial, fungal, acid, neutral or alkaline), amylases (alpha orbeta), lipases, mannanases, cellulases, collagenases, lisozymes, superoxide dismutase, catalase, and mixtures thereof. Said proteases include, but are not limited to, trypsin, chymotrypsin, pepsin, pancreatin and other mammalian enzymes; papain, bromelain and other botanical enzymes; subtilisin, epidermin, nisin, naringinase(L-rhammnosidase) urokinase and other bacterial enzymes. Said lipases include, but are not limited to, triacyl-glycerol lipases, monoacyl glycerol lipases, lipoprotein lipases, e.g. steapsin, erepsin, pepsin, other mammalian, botanical, bacterial lipases and purified ones. Natural papain is preferred as said enzyme. Further, stimulating hormones, e.g. insulin, can be used together with these enzymes to boost the effectiveness of them.

The pharmaceutically active ingredient may also be a sunscreen agent. The Sunscreen agent can be selected from any Sunscreen agent known in the art to protect skin from the harmful effects of exposure to sunlight. The sunscreen compound is typically chosen from an organic compound, an inorganic compound, or mixtures thereof that absorbs ultraviolet (UV) light. Thus, representative non limiting examples that can be used as the sunscreen agent include; aminobenzoic acid, cinoxate, diethanolamine methoxycinnamate, digalloyl trioleate, dioxybenzone, ethyl 4-bis(Hydroxypropyl) aminobenzoate, glyceryl aminobenzoate, homosalate, lawsone with dihydroxyacetone, menthyl anthranilate, octocrylene, octyl methoxycinnamate, octyl salicylate, oxybenzone, padimate O, phenylbenzimidazole sulfonic acid, red petrolatum, sulisobenzone, titanium dioxide, trolamine salicylate, cetarninosalol, allatoin, PABA, benzalphthalide, benzophenone, benzophenone 1-12, 3-benzylidene camphor, benzylidenecamphor hydrolyzed collagen sulfonamide, benzylidene camphor sulfonic acid, benzyl salicylate, bomelone, bumetriozole, butyl methoxydibenzoylmethane, butyl PABA, ceria/silica, ceria/silica talc, cinoxate, DEA-methoxycinnamate, dibenzoxazol naphthalene, di-t-butyl hydroxybenzylidene camphor, digalloyl trioleate, diisopropyl methyl cinnamate, dimethyl PABA ethyl cetearyldimonium tosylate, dioctyl butamido triazone, diphenyl carbomethoxy acetoxy naphthopyran, disodium bisethylphenyl tiamminotriazine stilbenedisulfonate, disodium sistyrylbiphenyl triaminotriazine stilbenedisulfonate, disodium distyrylbi phenyl disulfonate, drometrizole, drometrizole trisiloxane, ethyl dihydroxypropyl PABA, ethyl diisopropylcinnamate, ethyl methoxycinnamate, ethyl PABA, ethyl urocanate, etrocrylene ferulic acid, glyceryl octanoate dimethoxycin namate, glyceryl PABA, glycol salicylate, homosalate, isoamyl p-methoxycinnamate, isopropylbenzyl salicylate, isopropyl dibenzolylmethane, isopropyl methoxycinnamate, menthyl anthranilate, menthyl salicylate, 4-methylbenzylidene, camphor, octocrylene, octrizole, octyl dimethyl PABA, octyl methoxycinnamate, octyl salicylate, octyl triazone, PABA, PEG-25 PABA, pentyl dimethyl, PABA, phenylbenzimidazole sulfonic acid, polyacrylamidomethyl benzylidene camphor, potassium methoxycinnamate, potassium phenylbenzimidazole sulfonate, red petrolatum, sodium phenylbenzimidazole sulfonate, sodium urocanate, TEA-phenylbenzimidazole sulfonate, TEA-salicylate, terephthalylidene dicamphor sulfonic acid, titanium dioxide, zinc dioxide, serium dioxide, TriPABA panthenol, urocanic acid, and VA/crotonates/methacryloxybenzophenone-1 copolymer.

The Sunscreen agent can be a single one or combination of more than one. Alternatively, the Sunscreen agent is a cinnamate based organic compound, or alternatively, the Sunscreen agent is octyl methoxycinnamate, Such as Uvinul R. MC 80 an ester of para-methoxycinnamic acid and 2-ethyl hexanol.

Component (E) may also be a fragrance or perfume. The perfume can be any perfume or fragrance active ingredient commonly used in the perfume industry. These compositions typically belong to a variety of chemical classes, as varied as alcohols, aldehydes, ketones, esters, ethers, acetates, nitrites, terpenic hydrocarbons, heterocyclic nitrogen or Sulfur containing compounds, as well as essential oils of natural or synthetic origin. Many of these perfume ingredients are described in detail in standard textbook references such as Perfume and Flavour Chemicals, 1969, S. Arctander, Mont clair, N.J.

Fragrances may be exemplified by, but not limited to, perfume ketones and perfume aldehydes. Illustrative of the perfume ketones are buccoxime; isojasmone; methyl beta naphthyl ketone; musk indanone; tonalid/musk plus; Alpha Damascone, Beta-Damascone, Delta-Damascone, Iso Damascone, Damascenone, Damarose, Methyl Dihydrojasmonate, Menthone, Carvone, Camphor, Fenchone, Alpha-lonone, Beta-lonone, Gamma-Methyl So called lonone, Fleuramone, Dihydrojasmone, Cis-Jasmone, Iso-E-Super, Methyl-Cedrenyl-ketone or Methyl-Cedrylone, Acetophenone, Methyl-Acetophenone, Para-Methoxy-Acetophenone, Methyl-Beta-Naphtyl-Ketone, Benzyl-Acetone, Benzophenone, Para-Hydroxy-Phenyl-Butanone, Celery Ketone or LiveScone, 6-Isopropyldecahydro-2-naphtone, Dimethyl-octenone, Freskomenthe, 4-(1-Ethoxyvinyl)-3,3, 5.5-tetramethyl-Cyclohexanone, Methyl heptenone, 2-(2-(4-Methyl-3-cyclohexen-1-yl)propyl)-cyclopentanone, 1-(p-Menthen-6 (2)-yl)-1-propanone, 4-(4-Hydroxy-3-methoxyphenyl)-2-butanone, 2-Acetyl-3,3-Dimethyl Norbornane, 6,7-Dihydro-1,1,2,3,3-Pentamethyl-4(5H)-Indanone, 4-Damascol, Dulcinyl or Cassione, Gelsone, Hexylon, Isocyclemone E. Methyl Cyclocitrone, Methyl Lavender-Ketone, Orivon, Para-tertiary-Butyl-Cyclohexanone, Verdone, Delphone, Muscone, Neobutenone, Plica tone, Veloutone, 2,4,4,7-Tetramethyl-oct-6-en-3-one, and Tetrameran.

More preferably, the perfume ketones are selected for their odor character from Alpha Damascone, Delta Damascone, Iso Damascone, Carvone, Gamma-methyl-ionone, Iso-E-Super, 2.4.4.7-Tetramethyl-oct-6-en-3-one, Benzyl Acetone, Beta Damascone, Damascenone, methyl dihydrojasmonate, methyl cedrylone, and mixtures thereof.

Preferably, the perfume aldehyde is selected for its odor character from adoxal, anisic aldehyde, cymal, ethylvanillin, florhydral, helional, heliotropin, hydroxycitronellal, koavone, lauric aldehyde, lyral, methyl nonyl acetaldehyde, P. T. bucinal, phenyl acetaldehyde, undecylenic aldehyde, vanillin, 2,6,10-trimethyl-9-undecenal, 3-dodecen-1-al, alpha-n-amyl cinnamic aldehyde, 4-methoxybenzaldehyde, benzaldehyde, 3-(4-tert-butylphenyl)-propanal, 2-methyl-3-(para-methoxyphenyl propanal, 2-methyl-4-(2,6,6-trimethyl-2(1)-cyclohexen-1-yl) butanal, 3-phenyl-2-propenal, cis-/trans-3,7-dimethyl-2,6-octadien-1-al, 3,7-dimethyl-6-octen-1-al. (3,7-dimethyl-6-octenyl)oxyacetaldehyde, 4-isopropylbenzyaldehyde, 1,2,3,4,5,6,7,8-octahydro-8,8-dimethyl-2-naphthaldehyde, 2,4-dimethyl-3-cyclohexen-1-carboxaldehyde, 2-methyl-3-(isopropylphenyl)propanal, 1-decanal; decyl aldehyde, 2,6-dimethyl-5-heptenal, 4-(tricyclo[5.2.1.0(2,6)-decylidene-8)-butanal, octahydro-4,7-methano-1H-indenecarboxaldehyde, 3-ethoxy-4-hydroxy benzaldehyde, para-ethyl-alpha,alpha-dimethyl hydrocinnamaldehyde, alpha-methyl-3,4-(methylenedioxy)-hydrocinnamaldehyde, 3,4-methylenedioxybenzaldehyde, alpha-n-hexyl cinnamic aldehyde, m-cymene-7-carboxaldehyde, alpha-methyl phenyl acetaldehyde, 7-hydroxy-3,7-dimethyl octanal, Undecenal, 2,4,6-trimethyl-3-cyclohexene-1-carboxaldehyde, 4-(3)(4-methyl-3-pentenyl)-3-cyclohexen-carboxaldehyde, 1-dodecanal, 2,4-dimethyl cyclohexene-3-carboxaldehyde, 4-(4-hydroxy-4-methylpentyl)-3-cylohexene 1-carboxaldehyde, 7-methoxy-3,7-dimethyloctan-1-al, 2-methyl undecanal, 2-methyl decanal, 1-nonanal, 1-octanal, 2,6,10-trimethyl-5.9-undecadienal, 2-methyl-3-(4-tertbutyl) propanal, dihydrocinnamic aldehyde, 1-methyl-4-(4-methyl 3-pentenyl)-3-cyclohexene-1-carboxaldehyde, 5 or 6 methoxyl-hexahydro-4,7-methanoindan-1 or 2-carboxaldehyde, 3,7-dimethyloctan-1-al, 1-undecanal, 10-undecen-1-al, 4-hydroxy-3-methoxy benzaldehyde, 1-methyl-3-(4-methylpentyl)-3-cyclhexenecarboxaldehyde, 7-hydroxy-3,7-dimethyl octanal, trans-4-decenal, 2,6-nonadienal, paratolylacetaldehyde, 4-methylphenylacetaldehyde, 2-methyl-4-(2,6,6-trimethyl-1-cyclohexen-1-yl)-2-butenal, ortho-methoxycinnamic aldehyde, 3,5,6-trimethyl-3-cyclohexene carboxaldehyde, 3,7-dimethyl-2-methylene-6-octenal, phenoxyacetaldehyde, 5,9-dimethyl-4,8-decadienal, peony aldehyde (6,10-dimethyl-3-oxa-5,9-undecadien-1-al), hexahydro-4,7-methanoindan-1-carboxaldehyde, 2-methyloctanal, alpha-methyl- 4-(1-methylethyl)benzene acetaldehyde, 6,6-dimethyl-2-norpinene-2-propionaldehyde, para-methyl phenoxyacetaldehyde, 2-methyl-3-phenyl-2-propen-1-al, 3,5,5-trimethylhexanal, Hexahydro-8,8-dimethyl-2-naphthaldehyde, 3-propyl-bicyclo[2.2.1-hept-5-ene-2-carbaldehyde, 9-decenal, 3-methyl-5-phenyl-1-pentanal, methylnonyl acetaldehyde, hexanal, trans-2-hexenal, 1-pmenthene-q-carboxaldehyde and mixtures thereof. More preferred aldehydes are selected for their odor character from 1-decanal, benzaldehyde, florhydral, 2,4-dimethyl-3-cyclohexen-1-carboxaldehyde, cis/trans-3,7-dim ethyl-2,6-octadien-1-al, heliotropin, 2,4,6-trimethyl-3-cyclohexene-1-carboxaldehyde, 2,6-nonadienal, alphanamyl cinnamic aldehyde, alpha-n-hexyl cinnamic aldehyde, P. T. Bucinal, lyral, cymal, methylnonyl acetaldehyde, hexanal, trans-2-hexenal, and mixture thereof. In the above list of perfume ingredients, some are commercial names conventionally known to one skilled in the art, and also includes isomers. Such isomers are also suitable for use in the present invention.

Component (E) may also be one or more plant extract. Examples of these components are as follows: Ashitaba extract, avocado extract, hydrangea extract, Althea extract, Arnica extract, aloe extract, apricot extract, apricot kernel extract, Ginkgo Biloba extract, fennel extract, turmeric Curcuma extract, oolong tea extract, rose fruit extract, Echinacea extract, Scutellaria root extract, Phellodendro bark extract, Japanese Coptis extract, Barley extract, Hyperium extract, White Nettle extract, Watercress extract, Orange extract, Dehydrated saltwater, seaweed extract, hydrolyzed elastin, hydrolyzed wheat powder, hydrolyzed silk, Chamomile extract, Carrot extract, Artemisia extract, Glycyrrhiza extract, hibiscustea extract, Pyracantha Fortuneana Fruit extract, Kiwi extract, Cinchona extract, cucumber extract, guanocine, Gardenia extract, Sasa albomarginata extract, Sophora root extract, Walnut extract, Grapefruit extract, Clematis extract, Chlorella extract, mulberry extract, Gentiana extract, black tea extract, yeast extract, burdock extract, rice bran ferment extract, rice germ oil, comfrey extract, collagen, cowberry extract, Gardenia extract, Asiasarum root extract, Family of Bupleurum extract, umbilical cord extract, Salvia extract, Saponaria extract, Bamboo extract, Crataegus fruit extract, Zanthoxylum fruit extract, Shiitake extract, Rehmannia root extract, gromwell extract, Perilla extract, linden extract, Filipendula extract, peony extract, calamus root extract, white birch extract, Horsetail extract, Hedera Helix(Ivy) extract, hawthorn extract, Sambucus migra extract, Achillea millefolium extract, Mentha piperita extract, sage extract, mallow extract, Cnidium officinale root extract, Japanese green gen tian extract, Soybean extract, jujube extract, thyme extract, tea extract, clove extract, Gramineae imperata cyrillo extract, citrus unshiu peel extract Japanese angelica root extract, calendula extract, peach kernel extract, Bitter orange peel extract, Houttuyna cordata extract, tomato extract, natto extract, ginseng extract, green tea extract (camelliea sine sis), garlic extract, wild rose extract, hibiscus extract, Ophio pogon tuber extract, Nelumbo nucifera extract, parsley extract, honey, hamamelis extract, parietaria extract, isodonis herba extract, bisabolol extract, Loquat extract, coltsfoot extract, butterbur extract, Pond cocos wolf extract, extract of butcher's broom, grape extract, propolis extract, lufa extract, safflower extract, peppermintextract, linden tree extract, Paeonia extract, hop extract, pine tree extract, horse chestnut extract, Mizu-bashou Lysichiton camtschatcese extract, Mukurossi peel extract, Melissa extract, peach extract, corn flower extract, eucalyptus extract, saxifrage extract, citron extract, coix extract, mugwort extract, lavender extract, apple extract, lettuce extract, lemon extract, Chinese milk vetch extract, rose extract, rosemary extract, Roman Chamomile extract, and royal jelly extract.

The amount of component (E) present in the NIPU gel composition may vary, but typically range as follows: 0.05 to 50 wt %, alternatively 1 to 25 wt %, or alternatively 1 to 10 wt %, based on the amount by weight of NIPU elastomer gel present in the composition, that is total weight of components (A), (B), (C) and (D) in the NIPU gel composition.

The active, component (E), may be added to the NIPU gel composition either during the making of the NIPU elastomer (pre-load method), or added after the formation of the NIPU elastomer gel (post load method).

The pre-load method involves:

I) mixing:
   A) cyclic or aliphatic carbonate polymer, which may optionally contain siloxanes in its backbone;
   B) aliphatic or cycloaliphatic polyamine;
   C) an optional reaction catalyst;
   D) an optional carrier fluid, wherein the topically acceptable carrier fluid is a reaction solvent or wherein the carrier fluid is added after elastomer formation, optionally wherein the carrier fluid comprises a topically acceptable carrier fluid;
   E) a personal care or healthcare active with the NIPU elastomer gel to form the NIPU elastomer gel containing active.

The post-load method involves;

I) mixing:
   A) cyclic or aliphatic carbonate polymer, which may optionally contain siloxanes in its backbone;
   B) aliphatic or cycloaliphatic polyamine;
   C) an optional reaction catalyst;
   D) an optional carrier fluid, wherein the topically acceptable carrier fluid is a reaction solvent or wherein the carrier fluid is added after elastomer formation, optionally wherein the carrier fluid comprises a topically acceptable carrier fluid;

II) shearing the NIPU elastomer gel into a smooth paste; and

III) admixing:
   E) a personal care or healthcare active with the NIPU elastomer gel to form the NIPU elastomer gel containing active. The personal care active may also be admixed as a component of another mixture with one or more excipients.

The NIPU Elastomers

The NIPU elastomers of the present invention are obtainable as NIPU reaction products of components (A), (B), and (C) in (D). The term "NIPU reaction" means the addition of a compound containing multiple cyclic or non-cyclic carbonate groups (such as component A) to a compound containing multiple primary or secondary amine groups (such as component B), optionally in the presence of a catalyst (such as component C). Wherein the molar ratio of carbonate to amine groups is 1/1. Alternatively, this ratio can range from 8/1 to 0.9/1. The NIPU reaction is conducted in the presence of a solvent, where the solvent is the same as the carrier fluid described as component (D) and can optionally be used without further purification.

Methods for Measuring Hardness of NIPU Elastomer Gel Compositions

The NIPU elastomers are prepared in a carrier fluid (as described above as component D) to form gelled compositions. The gelled compositions of the present invention may be characterized by their hardness or firmness. Useful tests to characterize the gels are those recommended by the Gelatin Manufacturers Institute of America such as the use of a "Texture Analyzer" (model TAXT2, Stable Micro Systems, Inc., Godalming, England). The gel sample is subjected to a compression test with the Texture Analyzer having a probe with a 5.0 kg load cell. The probe approaches the surface of the gel at a speed of 1 mm/sec and continues compression into the gel to a distance of 5.0 mm. The Texture Analyzer detects the resistance force the probe experiences during the compression test. The force exhibited by the load cell is plotted as a function of time. The hardness of the NIPU elastomers, gels and elastomer blends (SEBs) for purposes of this invention is defined as the resistance force detected by the probe of the "Texture Analyzer" during the compression test. Hardness is characterized as the force at the maximum compression point (i.e. the 5.0 mm compression point into the gel Surface). The average of a total of 3 tests are typically performed for each gel and gels were made in triplicate.

The value obtained for force (in grams) is converted into Newtons (N), by dividing the gram force value by 101.97. (i.e. 1 Newton equals 101.97 g force based on the size of the probe used). The second property reported by Texture Analyzer measurement is Area F-T 1:2, in g force·sec. This is the area integration of the force vs. test time cure. This property is indicative of a gel network since it indicates ability to sustain resistance to the compression force, which is relevant to elastomers and gels. The value is reported in g force·sec and is converted to Newton·sec in SI unit by dividing the value in force·sec by 101.97.

The NIPU gels of the present invention have a compression hardness of at least 0.5 Newton/cm$^2$, alternatively 1 Newton/cm$^2$, or alternatively 2 Newton/cm$^2$ when measured with a 1.27 cm diameter spherical probe and a 50 g gel sample in a 4-ounce round glass jar.

Gel Paste Compositions Containing the NIPU Elastomer

The gelled compositions of the present invention can be used to prepare gel paste or gel blend compositions containing actives by:

I) shearing the NIPU elastomer gel, as described below,
II) combining the sheared NIPU elastomer gel with additional quantities of
  D) the carrier fluid, as described above, and optionally
  E) a personal or health care active to form a gel paste or blend composition. The personal care active may also be admixed as a component of another mixture with one or more excipients.

The NIPU elastomer gel compositions of the present invention may be considered as discrete crosslinked NIPU elastomer gel particles dispersed in carrier fluids. Thus, the NIPU elastomer compositions are effective rheological thickeners for compatible lower molecular weight solvents. As such they can be used to prepare useful gel blend compositions, such as "gel paste' compositions.

To make such NIPU elastomer gel pastes, the aforementioned NIPU elastomer gels of known initial elastomer content (IEC) are sheared to obtain small particle size and further diluted to a final elastomer content (FEC). Shearing, as used herein refers to any shear mixing process, such as obtained from homogenizing, sonolating, or any other mixing processes known in the art as shear mixing. The shear mixing of the NIPU elastomer gel composition results in a composition having reduced particle size. The subsequent composition having reduced particle size is then further combined with D) the carrier fluid. The carrier fluid may be any carrier fluid as described above, but typically is a linear ester (e.g. heptyl undecylenate), triglyceride (e.g. triheptanoin), or alkane (e.g. isododecane). The technique for combining D) the carrier fluid with the NIPU elastomer composition having reduced particle size is not critical, and typically involves simple stirring or mixing. The resulting compositions may be considered as a paste, having a viscosity greater than 100,000 cP (mPas).

Methods for Measuring Viscosity of NIPUElastomer Gel Pastes

The Brookfield HELIPATH™ Stand, when used with a suitable Brookfield Viscometer fitted with a special T-bar type spindle, will permit viscosity/consistency measurements in centipoise values for materials having characteristics similar to paste, putty, cream, gelatin, or wax. The viscosity of NIPU elastomer blends was determined using a Brookfield Model DV-II+Pro Viscometer with HELIPATH™ stand (Brookfield Model D) and T-Bar spindles (Brookfield Helipath Spindle Set). All were purchased from Brookfield Engineering Laboratories, Inc. (11 Commerce Boulevard Middleboro, Mass., USA). A sample size of 50 g in a 4-ounce round jar was required. The following preparation procedure was used before measurement: air bubbles were removed from samples first via centrifuge and then under vacuum for two hours. After de-airing, the sample was conditioned for a minimum of 4 hours at 25° C. The measurement was taken according to the typical procedure for a HELIPATH™ spindle. In general, spindle 93 (T-bar spindle E) is used and the standard setting for rpm was 6.5. The spindle speed is maintained at constant 6.5 rpm.

Topical formulations comprising the gel compositions or gel pastes are also provided herein. In such formulations, the gel compositions or gel pastes are suitably used as thickeners or stabilizers for the topical formulations. Other components of the topical formulations are known in the art, and can include for example, various components such as emulsion stabilizers, emulsifiers skin conditioners, suspending agents etc. The amounts of these additional components can be on the order of about 0.01% to about 50% by weight.

As used herein an "emulsion stabilizer" refers to a composition that aids in keeping an emulsion from separating into its oil and aqueous components. In embodiments, the emulsion stabilizer utilized in the formulations described herein is a naturally derived gum or a modified gum or natural mineral. Exemplary emulsion stabilizers include, but are not limited to, acacia, cellulose, crystalline cellulose, gellan, guar, locust (carob) bean, xanthan, magnesium aluminum silicate, bentonite or hectorite clays and the like, including combinations thereof.

As used herein a "skin conditioner" refers to a composition that acts as a lubricant on the surface of the skin or a composition that increases the water content of the surface of the skin. Exemplary skin conditioners for use in the formulations include, but are not limited to, adipate esters, alkyl benzoates, fatty acid esters of C8 or greater, esterified erucates, laurates, neopentanoates, salicylates, stearates, triglycerides, carbonates, glycols, glycerin, mineral oils and the like, including combinations thereof.

As used herein an "emulsifier" refers to a composition that aids in the formation of an oil in water, or a water in oil, emulsion. Exemplary emulsifiers for use in the formulations include, but are not limited to, polysorbates, ethoxylated fatty acids, fatty acids neutralized with sodium hydroxide, potassium hydroxide or amines, substituted glucosides, sodium lauryl and lauryl ether sulfates, ethoxylated esters, lecithin and lecithin derivatives and the like, including combinations thereof.

As used herein a "suspending agent" refers to a composition that modifies the interface between solid particles and a liquid medium to improve the particles' resistance to coming together and falling out of solution. Exemplary suspending agents for use in the formulations include, but are not limited to, hydroxy stearic acid, polyhydroxystearic acid, sodium polyacrylate polymers, methyl methacrylate crosspolymers and the like, including combinations thereof.

In additional embodiments, the non-isocyanate polyurethane (NIPU) elastomers can be utilized in solid-based formats, including for example, as a foot conforming shoe insert or shoe sole.

The non-isocyanate polyurethane (NIPU) elastomers can also be used as medically acceptable gels, including for example, medical implants or portions of implants, including as cartilage replacements, bone replacements, etc.

Exemplary Embodiments

Embodiment 1. A non-isocyanate polyurethane (NIPU) elastomer of Formula I:

Formula I

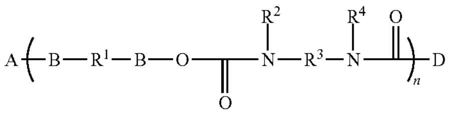

wherein:

n is 2 to m;

A is an end group selected from a cyclocarbonate and an amine;

B is selected from

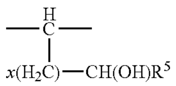 and $-(CH_2)_x-C(OH)R^5-$;

x is 0 to 4;

R1 is a C1-C30 substituted or unsubstituted linear or branched aliphatic group, cycloaliphatic group, aryl group, heterocycloaliphatic group, or heteroaryl group, optionally comprising a heteroatom;

R2, R4, and R5 are independently hydrogen or a C1-C30 substituted or unsubstituted linear or branched alkyl group, aliphatic group, cycloaliphatic group, or aryl group, optionally comprising a heteroatom;

R3 is a C1-C30 substituted or unsubstituted linear or branched aliphatic group, cycloaliphatic group, aryl group, heterocycloaliphatic group, or heteroaryl group, optionally comprising a heteroatom; and D is an end group selected from a cyclocarbonate and an amine, wherein m is a whole integer between 3 and 1,000,000,000,000, including 10, 100, 1,000, 10,000, 100,000, 1,000,000, 10,000,000, 100,000,000, 1,000,000,000, 10,000,000,000, 100,000,000,000 and 1,000,000,000,000, as well as other values between 3 and 1,000,000,000,000.

Embodiment 2. A gel composition comprising a non-isocyanate polyurethane (NIPU) elastomer prepared from the reaction of:

A) a polycarbonate or a mixture of polycarbonates comprising two or more carbonate functional groups;

B) a polyamine or mixture of polyamines comprising two or more amine functional groups, where the amine functional groups are either primary or secondary;

C) an optional NIPU reaction catalyst; and

D) an optional topically acceptable carrier fluid, wherein the topically acceptable carrier fluid is a reaction solvent or wherein the topically acceptable carrier fluid is added after elastomer formation, at a concentration of between 50% (w/w) and 99.9% (w/w) of the gel composition.

Embodiment 3. The gel composition of embodiment 2, wherein the topically acceptable carrier fluid is selected from the group consisting of esters, triglycerides, hydrocarbons, silicone fluids, and combinations thereof.

Embodiment 4. The gel composition of embodiment 2, wherein the topically acceptable carrier fluid is selected from the group consisting of diisooctyl succinate, heptyl undecylenate, neopentyl glycol diheptanoate, and coco caprylate.

Embodiment 5. The gel composition of embodiment 2, further comprising a pharmaceutically active ingredient dissolved in the topically acceptable carrier fluid.

Embodiment 6. The gel composition of embodiment 2, further comprising a pharmaceutically active ingredient incorporated in the gel.

Embodiment 7. The gel composition of embodiment 2 wherein the polycarbonate or mixture of polycarbonates is a low molecular weight polycarbonate or mixture of polycarbonates containing two or more hydroxyl groups and wherein the polyamine or mixture of polyamines is a low molecular weight polyamine or mixture of polyamines containing two or more primary or secondary amines.

Embodiment 8. A method of making a non-isocyanate polyurethane (NIPU) elastomer gel comprising:

i) mixing a polycarbonate reactant and a polyamine reactant, wherein the polycarbonate comprises two or more carbonate functional groups and the polyamine comprises two or more primary or secondary amines; and ii) optionally adding a topically acceptable carrier fluid, wherein the topically acceptable carrier fluid is a reaction solvent or wherein the topically acceptable carrier fluid is added after elastomer formation, to form a polymer gel mixture with a polymer concentration of about 80% (w/w); and iii) optionally adding a NIPU reaction catalyst; and iv) optionally heating the reaction mixture to about 100° C. to form the NIPU elastomer.

Embodiment 9. The method of embodiment 8, wherein the topically acceptable carrier fluid is selected from the group consisting of esters, triglycerides, hydrocarbons, silicone fluids, and combinations thereof.

Embodiment 10. The method of embodiment 8, wherein the topically acceptable carrier fluid is selected from the group consisting of diisooctyl succinate, heptyl undecylenate, neopentyl glycol diheptanoate, and coco caprylate.

Embodiment 11. The method of embodiment 8, further comprising dissolving a pharmaceutically active ingredient in the topically acceptable carrier fluid.

Embodiment 12. The method of embodiment 8, wherein the polycarbonate reactant comprises two or more hydroxyl groups.

Embodiment 13. The method of embodiment 8, further comprising preparing the polycarbonate reactant from a vegetable oil or mixture of vegetable oils containing two or more hydroxyl groups.

Embodiment 14. The method of embodiment 8, further comprising preparing the polycarbonate reactant from a copolymer of dilinoleic acid or mixture of copolymers of dilinoleic acid.

Embodiment 15. A method of making a NIPU elastomer gel paste comprising the steps of:

i) shearing the NIPU elastomer of embodiment 1;

ii) optionally adding additional quantities of the topically acceptable carrier fluid during shearing to produce a gel paste composition; and iii) optionally adding a pharmaceutically active ingredient.

Embodiment 16. An NIPU elastomer gel paste prepared by the embodiment 15.

Embodiment 17. A topical formulation comprising:

the gel composition of embodiment 5 or embodiment 6, wherein the pharmaceutically active ingredient is a personal care active ingredient or a healthcare active ingredient.

Embodiment 18. A topical formulation comprising:

the NIPU elastomer gel paste of embodiment 15, comprising a personal care active ingredient or a healthcare active ingredient.

Embodiment 19. A gel composition comprising a non-isocyanate polyurethane (NIPU) elastomer prepared from the reaction of:

A) a polycarbonate or a mixture of polycarbonates comprising two or more carbonate functional groups;

B) a polyamine or mixture of polyamines comprising two or more amine functional groups, where the amine functional groups are either primary or secondary;

C) an optional NIPU reaction catalyst; and

D) a carrier fluid, wherein the carrier fluid is a reaction solvent or wherein the carrier fluid is added after elastomer formation, at a concentration of between 60% (w/w) and 99.9% (w/w) of the gel composition.

Embodiment 20. A foot conforming shoe insert or shoe sole comprising:

the non-isocyanate polyurethane (NIPU) elastomer of embodiment 1 or the gel composition of embodiment 19.

Embodiment 21. A medical medically acceptable gel comprising:

the non-isocyanate polyurethane elastomer (NIPU) of embodiment 1 or the gel composition of embodiment 19.

Embodiment 22. A topical formulation comprising:

the NIPU elastomer of embodiment 1.

Embodiment 23. A gel composition comprising the non-isocyanate polyurethane (NIPU) elastomer of embodiment 1 and a topically acceptable carrier fluid, at a concentration of between 60% (w/w) and 99.9% (w/w) of the gel composition.

Embodiment 24. A method of making a NIPU elastomer gel paste comprising the steps of:

i) shearing the gel paste of embodiment 23;

ii) optionally adding quantities of the topically acceptable carrier fluid during shearing to produce a gel paste composition; and iii) optionally adding a pharmaceutically active ingredient.

Embodiment 25. A NIPU elastomer gel paste prepared by the method of embodiment 24.

Embodiment 26. A topical formulation comprising the gel composition of embodiment 24 or the NIPU elastomer gel paste of embodiment 25.

EXAMPLES

Example 1

Preparation of Castor Oil/Isophorone Diamine NIPU Elastomer

To a stainless steel or glass reaction vessel add a topically acceptable carrier fluid that can dissolve castor oil like diisooctyl succinate, (400 grams), castor oil (71.1 grams) with hydroxyl value of 166.87 mg/g, and dimethyl carbonate (20.97 grams, 1.1 equivalent with respect to moles of hydroxyl groups). Stir the reaction mixture at a temperature between 25° C. to about 100° C. for up to 8 hours before the addition of isophorone diamine (36.08 grams) with stirring. Once a homogenous mixture is obtained, pour 50 grams of the mixture into a 4-ounce glass jar. Cover the remainder of the reaction mixture and the 50-gram sample and heat to 75° C. for up to about 23 hours, at which point a translucent gel will form. The hardness of the 50-gram sample of gel is expected to be about 0.87 $N/cm^2$, as determined using a Stable Micro Systems Texture Analyzer with a 5-kilogram load cell, fitted with a TA-18B Stable Micro Systems probe, and inserted 5 mm into the gel surface.

Break the NIPU elastomer gel into smaller pieces, place in a metal container, and add a topically acceptable carrier fluid which may or may not be heptyl undecylenate before homogenization into a smooth gel paste with a desired viscosity using a Silverson L5M-A homogenizer with a 30 mm diameter rotor, Square Hole High Shear Screen, and operating at 4500 to 8000 revolutions per minute.

Example 2

Preparation of Castor Oil/Hexemethylenediamine NIPU Elastomer

To a stainless steel or glass reaction vessel add a topically acceptable carrier fluid that can dissolve castor oil like diisooctyl succinate (400 grams), castor oil (71.1 grams) with hydroxyl value of 166.87 mg/g, and dimethyl carbonate (20.97 grams, 1.1 equivalent with respect to moles of hydroxyl groups). Stir the reaction mixture at about 75° C. for up to 8 hours before the addition of hexamethylenediamine (24.62 grams) with stirring. Once a homogenous mixture is obtained, pour 50 grams of the mixture into a 4-ounce glass jar. Cover the remainder of the reaction mixture and the 50-gram sample and heat to 75° C. for up to 23 hours, at which point a translucent gel will form. The hardness of the 50-gram sample of gel is expected to be about 0.87 $N/cm^2$, as determined using a Stable Micro Systems Texture Analyzer with a 5-kilogram load cell, fitted with a TA-18B Stable Micro Systems probe, and inserted 5 mm into the gel surface.

Break the NIPU elastomer gel into smaller pieces, place in a metal container, and add a topically acceptable carrier fluid which may or may not be heptyl undecylenate before homogenization into a smooth gel paste with a desired viscosity using a Silverson L5M-A homogenizer with a 30 mm diameter rotor, Square Hole High Shear Screen, and operating at 4500 to 8000 revolutions per minute.

Example 3

Preparation of Castor Oil/Diamine NIPU Elastomer

To a stainless steel or glass reaction vessel add a topically acceptable carrier fluid that can dissolve castor oil like diisooctyl succinate (400 grams), castor oil (71.1 grams) with hydroxyl value of 166.87 mg/g, and dimethyl carbonate (20.97 grams, 1.1 equivalent with respect to moles of hydroxyl groups). Stir the reaction mixture at a temperature between 25° C. to about 100° C. for up to 8 hours before the addition of a diamine with stirring. Once a homogenous mixture is obtained, pour 50 grams of the mixture into a 4-ounce glass jar. Cover the remainder of the reaction mixture and the 50-gram sample and heat to 75° C. for up to 23 hours, at which point a translucent gel will form. The hardness of the 50-gram sample of gel is expected to be about 0.87 $N/cm^2$, as determined using a Stable Micro Systems Texture Analyzer with a 5-kilogram load cell, fitted with a TA-18B Stable Micro Systems probe, and inserted 5 mm into the gel surface.

Break the NIPU elastomer gel into smaller pieces, place in a metal container, and add a topically acceptable carrier fluid which may or may not be heptyl undecylenate before homogenization into a smooth gel paste with a desired viscosity using a Silverson L5M-A homogenizer with a 30 mm diameter rotor, Square Hole High Shear Screen, and operating at 4500 to 8000 revolutions per minute.

Example 4

Preparation of Castor Oil/Triamine NIPU Elastomer Gel

To a stainless steel or glass reaction vessel add a topically acceptable carrier fluid that can dissolve castor oil like diisooctyl succinate (400 grams), castor oil (71.1 grams) with hydroxyl value of 166.87 mg/g, and dimethyl carbonate (20.97 grams, 1.1 equivalent with respect to moles of hydroxyl groups). Stir the reaction mixture at a temperature between 25° C. to about 100° C. for up to 8 hours before the addition of a triamine with stirring. Once a homogenous mixture is obtained, pour 50 grams of the mixture into a 4-ounce glass jar. Cover the remainder of the reaction mixture and the 50-gram sample and heat up to 75° C. for up to about 23 hours, at which point a translucent gel will form. The hardness of the 50-gram sample of gel is expected to be about 0.87 $N/cm^2$, as determined using a Stable Micro Systems Texture Analyzer with a 5-kilogram load cell, fitted with a TA-18B Stable Micro Systems probe, and inserted 5 mm into the gel surface.

Break the NIPU elastomer gel into smaller pieces, place in a metal container, and add a topically acceptable carrier fluid which may or may not be heptyl undecylenate before homogenization into a smooth gel paste with a desired viscosity using a Silverson L5M-A homogenizer with a 30 mm diameter rotor, Square Hole High Shear Screen, and operating at 4500 to 8000 revolutions per minute.

Example 5

Preparation of Dilinoleic Acid/Propane Diol Copolymer Diamine NIPU Elastomer Gel To a stainless steel or glass reaction vessel add a topically acceptable carrier fluid that can dissolve dilinoleic acid/propane diol copolymer triheptanoin (up to about 400 grams), and dimethyl carbonate (1.1 equivalent with respect to moles of hydroxyl groups of the diol copolymer). Stir the reaction mixture at a temperature between 25° C. to about 100° C. for up to 8 hours before the addition of a diamine with stirring. Once a homogenous mixture is obtained, pour 50 grams of the mixture into a 4-ounce glass jar. Cover the remainder of the reaction mixture and the 50-gram sample and heat up to 75° C. for up to about 23 hours, at which point a translucent gel will form. The hardness of the 50-gram sample of gel is expected to be about 0.87 $N/cm^2$, as determined using a Stable Micro Systems Texture Analyzer with a 5-kilogram load cell, fitted with a TA-18B Stable Micro Systems probe, and inserted 5 mm into the gel surface.

Break the NIPU elastomer gel into smaller pieces, place in a metal container, and add a topically acceptable carrier fluid which may or may not be heptyl undecylenate before homogenization into a smooth gel paste with a desired viscosity using a Silverson L5M-A homogenizer with a 30 mm diameter rotor, Square Hole High Shear Screen, and operating at 4500 to 8000 revolutions per minute.

Example 6

Preparation of Dilinoleic Acid/Dilinoleic Diol Copolymer Diamine NIPU Elastomer Gel To a stainless steel or glass reaction vessel add a topically acceptable carrier fluid that can dissolve dilinoleic acid/propane diol copolymer like triheptanoin (up to about 400 grams), and dimethyl carbonate (1.1 equivalent with respect to moles of hydroxyl groups of the diol copolymer). Stir the reaction mixture at a temperature between 25° C. to about 100° C. for up to 8 hours before the addition of a diamine with stirring. Once a homogenous mixture is obtained, pour 50 grams of the mixture into a 4-ounce glass jar. Cover the remainder of the reaction mixture and the 50-gram sample and heat up to 75° C. for up to about 23 hours, at which point a translucent gel will form. The hardness of the 50-gram sample of gel is expected to be about 0.87 $N/cm^2$, as determined using a Stable Micro Systems Texture Analyzer with a 5-kilogram load cell, fitted with a TA-18B Stable Micro Systems probe, and inserted 5 mm into the gel surface.

Break the NIPU elastomer gel into smaller pieces, place in a metal container, and add a topically acceptable carrier fluid which may or may not be heptyl undecylenate before homogenization into a smooth gel paste with a desired viscosity using a Silverson L5M-A homogenizer with a 30 mm diameter rotor, Square Hole High Shear Screen, and operating at 4500 to 8000 revolutions per minute.

Example 7

Preparation of a Serum Containing an NIPU elastomer

Add an NIPU elastomer gel (700 g) from one of the Examples 1 to 6 to a stainless steel reaction vessel that is equipped with an overhead stirrer. Add to this gel up to 300 g of argan oil and stir the mixture in the presence or absence of heat for up to 1 h to yield an argan serum Example 8

Preparation of an Oil in Water Emulsion with the NIPU Elastomer

An oil in water emulsion may be formed by adding a topically acceptable oil to the water phase with gentle heating to 75° C. Once cooled to room temperature, the NIPU elastomer may be post-added to a concentration between 5 and 90% to yield an elegant cream Example 9

Preparation of Sunscreen Composition Containing Castor Oil/Isophorone Diamine NIPU Elastomer Add Avobenzone (30 g; 3% w/w)+Octocrylene (100 g; 10% w/w)+Homosalate (150 g; 15% w/w)+Octylsalicylate (50 g; 5% w/w)+Sunboost (50 g; 5% w/w; Kobo)+Halbrite (50 g; 5% w/w; Hallstar), Vegelight (270 g; 27% w/w) and Castor Oil/Isophorone diamine NIPU elastomer gel paste (300 g; 30% w/w) to a stainless steel vessel and mix with an overhead mixer fitted with a paddle blade for 20 min to provide a homogenous sunscreen formulation.

Example 10

Preparation of a Dilinoleic Diol/Polyoxypropylenetriamine NIPU Elastomer

To a 4 ounce glass jar was added dilinoleic diol dimethyl dicarbonate (25.0 g), which was previously synthesized by the reaction of dilinoleic diol and dimethyl carbonate, and Jeffamine T-403 (12.65 g; Huntsman International LLC, The Woodlands, Tex.). The reaction mixture was stirred at room temperature until homogenous, at which time triazabicyclodecene (753 mg) was added. The colorless and clear reaction mixture was heated overnight at to 120° C. to yield a slightly tinted clear non-pourable elastomer rubber with a hardness of 180 $N/cm^2$, as determined using a Stable Micro Systems Texture Analyzer with a 5-kilogram load cell, fitted with a TA-18B Stable Micro Systems probe, and inserted 5 mm into the gel surface.

Example 11

Preparation of a Castor Oil/Isophorone Diamine NIPU Elastomer

To a test tube was added castor oil carbonate (500 mg), which was previously synthesized by the reaction of castor oil and dimethyl carbonate, and isophorone diamine (247 mg). The reaction mixture was vortexted at room temperature until homogenous, at which time triazabicyclodecene (12.47 mg) was added. The reaction mixture was heated to 120° C. in a heat block and vortexed to ensure homogenous mixture. The reaction mixture was heated overnight at 120° C. to yield a slightly non-pourable elastomer rubber with a hardness of 250 $N/cm^2$, as determined using a Stable Micro Systems Texture Analyzer with a 5-kilogram load cell, fitted with a TA-18B Stable Micro Systems probe, and inserted 5 mm into the gel surface.

Example 12

Preparation of a Dilinoleic Diol/Polyoxypropylenetriamine NIPU Elastomer Gel Paste The dilinoleic diol/polyoxypropylenetriamine NIPU elastomer of Example 10 was broken into small pieces using a hand tool and 24.65 g of the elastomer solids was added to a stainless steel reaction vessel followed by the addition of 24.65 g of diisooctyl succinate. The slurry was homogenized into a smooth gel paste after 5 minutes of mixing using a Silverson L5M-A homogenizer with a 30 mm diameter rotor, Square Hole High Shear Screen, and operating at 5000 revolutions per minute. The viscosity of the resultant smooth gel was 62,333 cps as measured using a spindle Brookfield Model DV-II+Pro Viscometer with Helipath stand (Brookfield Model D) and Spindle TC. The measurement was taken according to the typical procedure for a Helipath spindle with a constant spindle speed maintained at 6.5 rpm and torque of 37.4%.

The invention claimed is:

1. A gel composition comprising a non-isocyanate polyurethane (NIPU) elastomer being a reaction product of:

A) a polycarbonate or a mixture of polycarbonates comprising two or more carbonate functional groups;

B) a polyamine or mixture of polyamines comprising two or more amine functional groups, where the amine functional groups are either primary or secondary;

C) an NIPU reaction catalyst; and

D) a topically acceptable carrier fluid, wherein the topically acceptable carrier fluid is a reaction solvent at a concentration of between 50% (w/w) and 99.9% (w/w) of the gel composition; and wherein particles of the non-isocyanate polyurethane (NIPU) elastomer are dispersed in the topically acceptable carrier fluid;

wherein the gel composition further comprises a pharmaceutically active ingredient, the pharmaceutically active ingredient being dissolved in the topically acceptable carrier fluid, or the pharmaceutically active ingredient being incorporated in the gel; and wherein the gel composition further comprises an oil phase and a water phase.

2. The gel composition of claim 1, wherein the topically acceptable carrier fluid is selected from the group consisting of esters, triglycerides, hydrocarbons, silicone fluids, diisooctyl succinate, heptyl undecylenate, neopentyl glycol diheptanoate, and coco caprylate, and combinations thereof.

3. The gel composition of claim 1 wherein the polycarbonate or mixture of polycarbonates is a low molecular weight polycarbonate or mixture of polycarbonates containing two or more hydroxyl groups and wherein the polyamine or mixture of polyamines is a low molecular weight polyamine or mixture of polyamines containing two or more primary or secondary amines.

4. A topical composition:

the gel composition of claim 1, wherein the pharmaceutically active ingredient is a personal care active ingredient or a healthcare active ingredient.

5. The gel composition of claim 1, wherein the topically acceptable carrier fluid, is at a concentration of between 60% (w/w) and 99.9% (w/w) of the gel composition.

6. A topical formulation comprising the gel composition of claim 5.

7. The gel composition of claim 1, further comprising an emulsifier.

8. The gel composition of claim 1, wherein the pharmaceutically active ingredient comprises sunburn prevention and treatment agents.

* * * * *